(12) United States Patent
Piispanen

(10) Patent No.: US 11,192,065 B2
(45) Date of Patent: Dec. 7, 2021

(54) METHOD AND APPARATUS FOR SEPARATING CARBON DIOXIDE AND FOR UTILIZING CARBON DIOXIDE

(71) Applicant: Soletair Power Oy, Lappeenranta (FI)

(72) Inventor: Ari Piispanen, Lappeenranta (FI)

(73) Assignee: Soletair Power Oy, Lappeenranta (FI)

( * ) Notice: Subject to any disclaimer, the term of this patent is extended or adjusted under 35 U.S.C. 154(b) by 689 days.

(21) Appl. No.: 15/998,924

(22) PCT Filed: Feb. 16, 2017

(86) PCT No.: PCT/FI2017/050100
§ 371 (c)(1),
(2) Date: Aug. 16, 2018

(87) PCT Pub. No.: WO2017/140954
PCT Pub. Date: Aug. 24, 2017

(65) Prior Publication Data
US 2021/0205755 A1    Jul. 8, 2021

(30) Foreign Application Priority Data

Feb. 18, 2016   (FI) ..................................... 20165119

(51) Int. Cl.
*B01D 53/62*    (2006.01)
*B01D 53/73*    (2006.01)
(Continued)

(52) U.S. Cl.
CPC ............. *B01D 53/62* (2013.01); *B01D 53/73* (2013.01); *C07C 1/12* (2013.01); *C25B 1/04* (2013.01);
(Continued)

(58) Field of Classification Search
CPC ........ A61L 9/00; A61L 9/015; A61L 2101/00; A61L 2202/00; A61L 2202/10;
(Continued)

(56) References Cited

U.S. PATENT DOCUMENTS 10,968,410 B2 *   4/2021   Kim ........................ C10L 3/08
2009/0002203 A1    9/2009   Monzyk et al.
(Continued)

FOREIGN PATENT DOCUMENTS

CN        2612442 Y    4/2004
CN        1563820 A    1/2005
(Continued)

OTHER PUBLICATIONS

Chinese Office Action for corresponding Chinese Patent Application No. 201780011916.9 dated Dec. 27, 2019, 9 pages.
(Continued)

*Primary Examiner* — Timothy C Vanoy
(74) *Attorney, Agent, or Firm* — Merchant & Gould P.C.

(57) ABSTRACT

The invention relates to a method and to an apparatus for separating and utilizing carbon dioxide. According to the invention, carbon dioxide (3a, 3b) is separated from air (1a) being conducted to a building and/or from air (1c, 1d) being circulated in the building to reduce the level of carbon dioxide in indoor air (1b) of the building (4), the carbon dioxide (3a, 3b) is recovered, and the carbon dioxide is conducted to a carbon dioxide treatment stage (5), where a chemical compound (6) is formed from the carbon dioxide. In addition, the invention relates to the use of the method.

15 Claims, 3 Drawing Sheets

Figure 1:
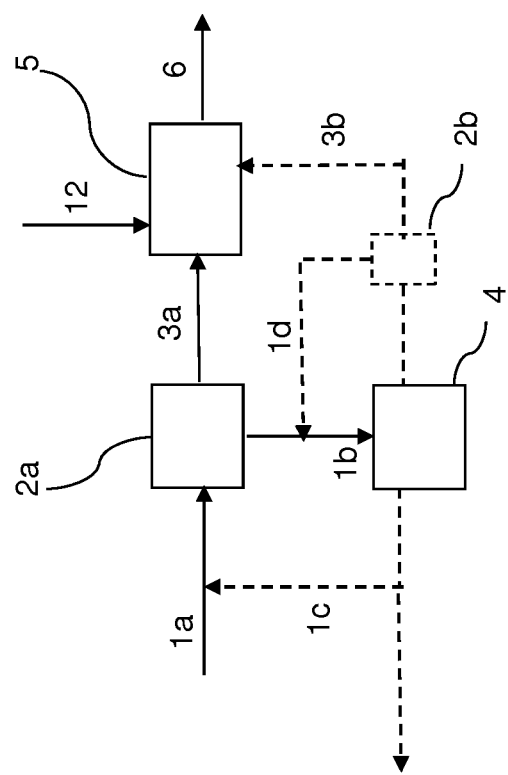

(51) Int. Cl.
*C07C 1/12* (2006.01)
*C25B 1/04* (2021.01)
*C07C 9/04* (2006.01)

(52) U.S. Cl.
CPC .. *B01D 2251/202* (2013.01); *B01D 2257/504* (2013.01); *B01D 2259/4508* (2013.01); *C07C 9/04* (2013.01)

(58) Field of Classification Search
CPC ............. A61L 2202/25; A61L 2209/10; A61L 2209/20; A61L 2209/213; B01D 2221/02; B01D 2221/16; B01D 2251/202; B01D 2257/504; B01D 2258/06; B01J 12/00; B01J 2219/0877; Y02A 30/00; Y02B 90/00; Y02C 20/40
See application file for complete search history.

(56) References Cited

U.S. PATENT DOCUMENTS

| | | |
|---|---|---|
| 2009/0289227 A1 | 11/2009 | Rising |
| 2011/0277490 A1 | 11/2011 | Meirav |
| 2012/0279397 A1 | 11/2012 | Wright et al. |
| 2013/0034487 A1 | 2/2013 | Tai et al. |
| 2014/0179810 A1 | 6/2014 | Yoon |
| 2016/0039724 A1* | 2/2016 | Naterer .................. C01B 3/063 422/142 |

FOREIGN PATENT DOCUMENTS

| | | |
|---|---|---|
| CN | 1723074 A | 1/2006 |
| CN | 103119376 A | 5/2013 |
| JP | H06-11106 A | 1/1994 |
| JP | 2004-261757 A | 9/2004 |
| WO | WO 2009/126607 A2 | 10/2009 |
| WO | WO 2013 029 701 A1 * | 3/2013 |

OTHER PUBLICATIONS

Extended European Search Report for European Patent Application No. 17752734.8 dated Aug. 30, 2019, 8 pages.
International Search Report for corresponding International Patent Application No. PCT/FI2017/050100 dated May 15, 2017, 6 pages.
Written Opinion of the International Searching Authority for corresponding International Patent Application No. PCT/FI2017/050100 dated May 15, 2017, 7 pages.
Finnish Search Report for corresponding Finnish Patent Application No. 20165119 dated Jun. 29, 2016, 1 page.

* cited by examiner

METHOD AND APPARATUS FOR SEPARATING CARBON DIOXIDE AND FOR UTILIZING CARBON DIOXIDE

This application is a National Stage Application of PCT/FI2017/050100, filed 16 Feb. 2017, which claims benefit of Application Serial No. 20165119, filed 18 Feb. 2016 in Finland, and which applications are incorporated herein by reference. To the extent appropriate, a claim of priority is made to each of the above disclosed applications.

FIELD OF THE INVENTION

The invention relates to a method defined in claim 1 and to an apparatus defined in claim 14 for separating and utilizing carbon dioxide, and to the use of the method defined in claim 18.

BACKGROUND OF THE INVENTION

Various methods are known in the prior art for separating and recovering carbon dioxide from gaseous material or gaseous stream.

It is also known that carbon dioxide is detrimental to health at high levels. The problem is that in the indoor air of buildings the level of carbon dioxide often rises high. In addition, in large cities the level of carbon dioxide in air is constantly very high, also outdoors.

OBJECTIVE OF THE INVENTION

The objective of the invention is to disclose a new method for separating carbon dioxide from air of a building and for recovering and utilizing the carbon dioxide. In addition, the objective of the invention is to disclose a method for reducing the level of carbon dioxide in buildings and for improving the quality of indoor air. In addition, the objective of the invention is to disclose a new apparatus to provide the improvement of the quality of indoor air. In addition, the objective of the invention is to disclose an energy-efficient assembly for separating carbon dioxide from air of a building and for utilizing the separated carbon dioxide.

SUMMARY OF THE INVENTION

The method and the apparatus according to the invention are characterized by the features presented in the claims.

In the method according to the invention, carbon dioxide, $CO_2$, is separated from air being conducted to a building and/or from air being circulated in a building to reduce the level of carbon dioxide in indoor air of the building, the carbon dioxide is recovered, and the carbon dioxide is conducted to a carbon dioxide treatment stage, where a chemical compound is formed from the carbon dioxide. Thus the air being conducted as indoor air to the building can be treated and cleaned, and the level of carbon dioxide of indoor air of the building can be reduced, and thereby the quality of indoor air of the building can be improved. In addition, the separated carbon dioxide can be recovered and utilized. From the carbon dioxide, chemical products can be manufactured by various processes suited for the intended application.

In addition, the invention is based on an apparatus which comprises at least one separating device for separating carbon dioxide from air being conducted to a building and/or from air being circulated in a building to reduce the level of carbon dioxide in indoor air of the building, at least one set of means for arranging the treated air as indoor air of the building, at least one carbon dioxide treatment stage which comprises at least one treatment device and where a chemical compound is formed from the carbon dioxide, and at least one set of means for recovering carbon dioxide from the separating device and for conducting it to the treatment stage. In addition, the apparatus may comprise at least one feeding device for conducting air to the building. In addition, the apparatus may comprise at least one set of circulating means for circulating air in the building, such as for circulating exhaust air of the building back as the indoor air of the building.

In this connection, a building is intended to mean any real property or building, such as a residential building, industrial building, hall, office space, public building or other such building.

In this connection, air being conducted to a building is intended to mean any air being conducted for use as indoor air of the building, wherein the air may be derived directly from the atmosphere, or atmospheric air may have been pretreated in a certain way before being conducted to the building. In one embodiment, the air is intended to mean air flowing to the ventilation system, e.g. a mechanical ventilation system, of the building.

In this connection, air being circulated in a building is intended to mean any circulating air or exhaust air of the building being circulated or returned back as indoor air of the building. The portion of air being circulated in the indoor air of the building may vary between 0 and 100%. The air being circulated may be treated and/or cleaned in addition to separating the carbon dioxide, e.g. by removing water or moisture.

The separation of carbon dioxide from air may be carried out by means of any separating device which is known per se in the art and which is suited for the intended purpose. The separating device may be any separating or recovery device known per se, wherein the separation of carbon dioxide from air may be based on a chemical method, a physical method, an absorption method, a dissolution method, a membrane method, other suitable method or combinations thereof. In one embodiment, the separation of carbon dioxide from air may be carried out by means of a scrubber. In one embodiment, the separation of carbon dioxide from air may be carried out by means of a solid chemically active agent. As the feeding device for feeding the air to the separating device, there may be used any device or means which is suited for the intended purpose and which is known in the art for conducting or sucking air to or through the separating device.

The air from which carbon dioxide has been removed can be fed or conducted from the separating device for use as indoor air of the building by any suitable means known per se, e.g. by a pipe, a coupling, a feeding device or combinations thereof. As the means for recovering carbon dioxide from the separating device and for conducting it to the treatment stage, there may be used any means which is known per se and which is suited for the intended purpose, e.g. an exhaust pipe, an exhaust coupling, a recovery device, a feeding device or other such means or combinations thereof.

In one embodiment, carbon dioxide is separated from air being conducted to the building and from air being circulated in the building to reduce the level of carbon dioxide in indoor air of the building. In one embodiment, the air being circulated is air being exhausted from the building and conducted and mixed to the air being conducted to the building before the separating stage, and carbon dioxide is separated from the mixture of the air being conducted to the building and the air being circulated in the building. In one embodiment, the air being circulated is air being exhausted from the building, from which carbon dioxide is separated, and the treated air is conducted for use as indoor air of the building or mixed to the indoor air being conducted to the building. In one embodiment, carbon dioxide is separated from air being conducted to the building. In one embodiment, carbon dioxide is separated from air being circulated in the building.

In one embodiment, the level of carbon dioxide of the air being conducted for use as indoor air of the building is adjusted to be below 800 ppm, in one embodiment below 700 ppm, in one embodiment below 600 ppm, by means of the separation of carbon dioxide. Thus, the level of carbon dioxide is at an appropriate level in terms of health in indoor air of the building. A high level of carbon dioxide in indoor air has a tiring effect and reduces stamina.

In one embodiment, water is removed from air being conducted to the building and/or from air being circulated in the building in connection with separation of the carbon dioxide. Thus the humidity of indoor air of the building can be reduced. In one embodiment, moisture is removed by means of heat, e.g. by means of a heat exchanger. The water removed may be recovered and utilized, or alternatively piped as wastewater. In one embodiment, the water removed from air may be conducted to hydrogen formation, such as to electrolysis. In one embodiment, the apparatus comprises at least one set of means for removing water from air being conducted to the building and/or from air being circulated in the building in connection with the carbon dioxide separating device.

In one embodiment, oxygen is conducted to air being conducted to the building and/or to air being circulated in the building or to the indoor air of the building in connection with or after the separation of carbon dioxide.

Preferably, carbon dioxide is recovered and fed to the carbon dioxide treatment stage. In one embodiment, carbon dioxide is treated in the treatment stage by means of a hydrogen treatment, such as by means of hydrogen, in order to form a chemical compound. In one embodiment, heat generated in the carbon dioxide treatment stage is conducted to the carbon dioxide separating stage. In one embodiment, heat generated in the carbon dioxide treatment stage is conducted to the heating of the building, e.g. to the tap water of the building.

In one embodiment, in the carbon dioxide treatment stage a chemical compound, such as an organic and/or inorganic compound, is formed from carbon dioxide. In one embodiment, in the carbon dioxide treatment stage hydrocarbon is formed. In one embodiment, in the carbon dioxide treatment stage methane ($CH_4$) is formed. In one embodiment, in the carbon dioxide treatment stage other suitable hydrocarbon is formed. In one embodiment, in the carbon dioxide treatment stage an oxygen containing compound is formed. In one embodiment, in the carbon dioxide treatment stage an alcohol based compound, such as methanol, is formed. In one embodiment, the treatment of carbon dioxide is carried out by means of chemical synthesis either in the presence of a catalyst or without a catalyst. In the carbon dioxide treatment stage there may be used any device which is known per se in the art and which is suited for the intended purpose, the device being preferably arrangeable under conditions, e.g. pressure and temperature, that are suitable in terms of the process or synthesis.

In one embodiment, the chemical compound, e.g. hydrocarbon, produced in the carbon dioxide treatment stage is recovered or processed further. In one embodiment, in the carbon dioxide treatment stage hydrocarbon, e.g. methane ($CH_4$), is formed to be used as fuel or as energy raw material or alternatively to be conducted for further processing, e.g. into longer chain hydrocarbon, a hydrocarbon based compound, a polymer, a plastic or other suitable compound or product. The further processing may be carried out by any manner which is known per se and which is suited for the intended purpose. In one embodiment, the further processing of the chemical compound, such as hydrocarbon, is carried out by means of chemical synthesis, Fischer Tropsch (FT) synthesis, other suitable synthesis, polymerization, other suitable treatment or combinations thereof.

In one embodiment, the method comprises a hydrogen formation stage. In one embodiment, hydrogen is formed from water. In one embodiment, hydrogen is formed from water by electrolysis. In one embodiment, the apparatus comprises an electrolysis device for forming hydrogen from water. In this connection there may be used any suitable electrolysis method and device known in the art for forming hydrogen. In one embodiment, the water produced in the treatment of carbon dioxide is conducted to the formation of hydrogen. In one embodiment, the water removed from air being conducted to the building and/or from air being circulated in the building is conducted to the formation of hydrogen. Alternatively, the water required for the formation of hydrogen may be derived from any suitable source, e.g. from a water supply network, a rainwater system or an exhaust air system or other suitable source. In one embodiment, the apparatus comprises at least one set of means for conducting water produced in the treatment of carbon dioxide or water removed from air being conducted to the building and/or from air being circulated in the building to the formation of hydrogen, such as to an electrolysis device.

In one embodiment, the hydrogen formed is conducted to the carbon dioxide treatment stage. In one embodiment, the apparatus comprises means for conducting hydrogen from electrolysis to the carbon dioxide treatment stage. In one embodiment, the hydrogen formed is fed to the manufacture of a chemical compound, e.g. an inorganic or organic chemical compound. In one embodiment, the hydrogen formed is fed to the manufacture of a hydrocarbon compound. In one embodiment, hydrogen formed is conducted to the manufacture of an ammonia based compound. In one embodiment, ammonia may be manufactured from hydrogen and nitrogen of the air. In one embodiment, from the ammonia based compound other nitrogen containing compounds are formed by further processing.

In one embodiment, heat generated in the formation of hydrogen is conducted to the carbon dioxide separating stage. In one embodiment, heat generated in the formation of hydrogen is conducted to the heating of the building, e.g. to the tap water of the building.

In one embodiment, oxygen produced in the formation of hydrogen is conducted to air being conducted to the building, to air being circulated in the building and/or to the indoor air. In one embodiment, the apparatus comprises means for conducting oxygen from the formation of hydrogen to air being conducted to the building, to air being circulated in the building and/or to the indoor air. In one embodiment, the oxygen produced in the formation of hydrogen is a product which is recovered. The oxygen can be used as a product, e.g. as bottled oxygen or industrial oxygen.

In one embodiment, so called surplus electricity is used as electricity required for the formation of hydrogen, when electricity is formed in excess relative to electricity consumption. In one embodiment, electricity generated in a wind power device or a solar cell device is used as electricity required for the formation of hydrogen. In one embodiment, electrolysis serves as a buffer of electricity production, whereby the electrolysis stage is implemented when there is surplus electricity.

In one embodiment, carbon dioxide separated from air being conducted to the building and/or from air being circulated in the building is conducted to a separate chemical process, to a storage, or back to the ambient air.

In one embodiment, the apparatus comprises a shell structure, e.g. walls, a floor and a ceiling, inside of which the components of the apparatus are arrangeable. In one embodiment, the apparatus may be arranged in a transportation container or other such easily moveable and/or transportable space. In one embodiment, the apparatus functions as a separate unit which is easily moveable and/or arrangeable to the target site.

The method and the apparatus according to the invention may be used in the treatment of indoor air of a building, in the manufacture of hydrocarbons, in the manufacture of hydrogen and in combinations thereof. The method and the apparatus according to the invention may be used in conjunction with any building.

The method according to the invention is integratable with the ventilation system, e.g. a mechanical ventilation system, of the building. The apparatus according to the invention is connectable so that it functions in conjunction with the ventilation system of the building.

By means of the invention, the indoor air of any building can be improved by removing carbon dioxide from it. Air being conducted to a building can be treated and the quality of indoor air improved in large and small buildings with the apparatus according to the invention. By means of the invention, the indoor air of small sites can also be cleaned flexibly and efficiently. By means of the invention, the degree of intake air and ventilation can also be reduced in a building, and thus the need of heating or cooling energy, and thereby the operating costs, of ventilation can be decreased.

In addition, hydrocarbons can be cost-effectively produced and non-fossil energy economically generated by the method and the apparatus according to the invention.

The apparatus according to the invention may be connected to buildings easily and cost-effectively.

LIST OF FIGURES

Figure 2:
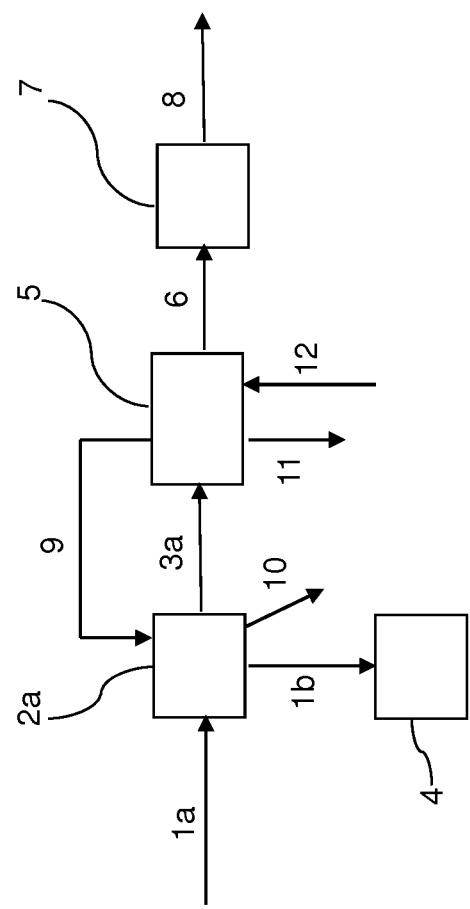
Figure 3:
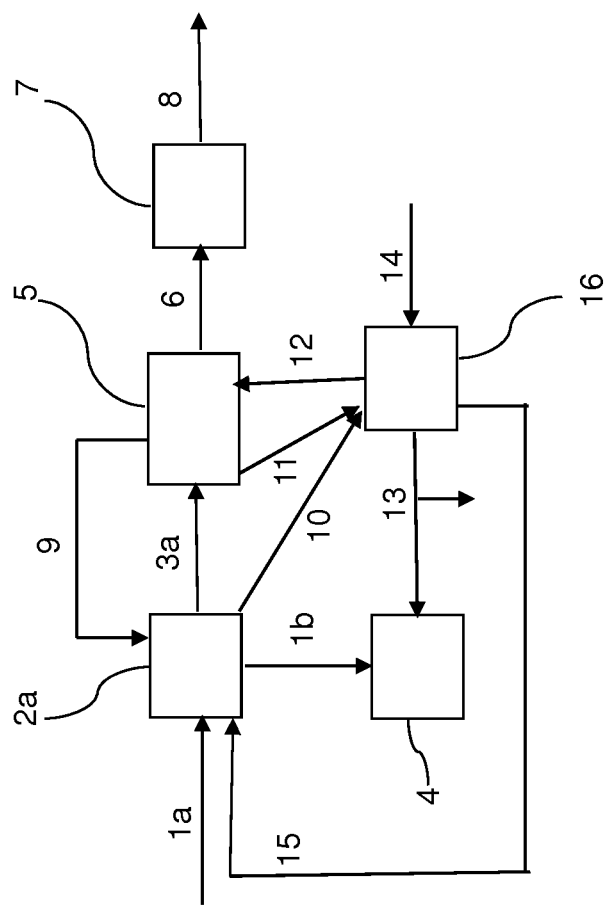

FIG. 1 presents one apparatus according to the invention,
FIG. 2 presents another apparatus according to the invention, and
FIG. 3 presents another apparatus according to the invention.

DETAILED DESCRIPTION OF THE INVENTION

The invention will be described below by way of detailed examples of its embodiments with reference to the accompanying figures.

Example 1

FIG. 1 presents an apparatus for separating and recovering carbon dioxide from air being conducted to a building and/or from air being circulated in a building and for utilizing the carbon dioxide.

In the apparatus of FIG. 1, carbon dioxide, $CO_2$, (3a,3b) is separated from air (1a) being conducted to a building, and additionally or optionally from air (1c,1d) being circulated in the building, by means of a carbon dioxide separating device (2a), and optionally by means of a separating device (2b), to reduce the level of carbon dioxide in indoor air (1b) of the building (4). The carbon dioxide (3a,3b) is recovered and conducted to a carbon dioxide treatment stage (5). The apparatus comprises a separating device (2a,2b) for separating carbon dioxide (3a,3b) from air (1a) being conducted to a building and/or from air (1c,1d) being circulated in the building, means for arranging the treated air as indoor air (1b) of the building, and a carbon dioxide treatment stage (5) which comprises a treatment device in order to form a chemical compound (6) from carbon dioxide by means of hydrogen treatment and hydrogen (12). In addition, the apparatus comprises means for recovering the carbon dioxide from the separating device and for conducting it to the treatment stage (5). In addition, the apparatus may comprise a feeding device for feeding the air (1a) to the separating device (2a).

In one embodiment, the level of carbon dioxide of the indoor air (1b) being fed to the building (4) is adjusted to be below 700 ppm by means of the separation of carbon dioxide.

Example 2

FIG. 2 presents an apparatus for recovering carbon dioxide from air being conducted to a building and for utilizing it in the manufacture of a chemical compound. FIG. 3 presents an apparatus for recovering carbon dioxide from air being conducted to a building and for utilizing it in the manufacture of a chemical compound and for the manufacture of hydrogen. By the apparatuses as shown in FIGS. 2 and 3 the level of carbon dioxide of indoor air of the building can be reduced.

The apparatuses of FIGS. 2 and 3 comprise a separating device (2a) of the type presented in Example 1 and in FIG. 1 for separating carbon dioxide (3a) from air (1a) being conducted to a building (4). In addition, the apparatuses comprise means for recovering the carbon dioxide (3a) and for conducting it to a treatment stage (5). The treatment stage (5) comprises at least one treatment device in order to form a chemical compound (6) by means of hydrogen (12). Organic compounds, such as methane or methanol, can be manufactured from the carbon dioxide by means of hydrogen treatment. The organic compounds may be processed further (7) into target compounds (8). In addition, the apparatus comprises means for conducting heat (9) generated in the carbon dioxide treatment stage (5) to the carbon dioxide separating device (2a). In addition, the apparatus comprises means for removing water (10) from the air (1a) being conducted to the building in connection with the carbon dioxide separation (2a), and removal means for removing water (11) produced in the carbon dioxide treatment stage (5).

In addition, the apparatus of FIG. 3 comprises an electrolysis device (16) for forming hydrogen (12) from water. Hydrogen can be manufactured from water by means of electrolysis, wherein the electrolysis can be carried out in a manner known per se. Electricity (14) required for the electrolysis may preferably be surplus electricity of electricity production e.g. from a wind power device or a solar cell device. In addition, the apparatus comprises means for removing water (10) from the air (1a) being conducted to the building in connection with the carbon dioxide separation (2a), and means for conducting the water to the electrolysis (16). In addition, the apparatus comprises means for conducting water (11) produced in the carbon dioxide treatment stage (5) to the electrolysis (16). In addition, the apparatus comprises means for conducting hydrogen (12) from the electrolysis (16) to the carbon dioxide treatment stage (5). In addition, the apparatus may comprise means for feeding hydrogen to the manufacture of ammonia, where ammonia is manufactured from hydrogen and nitrogen of the air.

In addition, the apparatus (FIG. 3) comprises means for conducting heat (15) generated in the electrolysis (16) to the carbon dioxide separating device (2a) and means for conducting oxygen (13) to indoor air (1b) of the building from the electrolysis (16).

The method and the apparatus according to the invention are suited as different embodiments for use in a variety of applications for separating and also recovering carbon dioxide as well as for treating and cleaning the indoor air of a building. In addition, the method and the apparatus according to the invention are suited as different embodiments for use in the manufacture of a variety of chemical compounds. In addition, the method and the apparatus according to the invention are suited as different embodiments for use in connection with a variety of processes utilizing carbon dioxide.

The invention is not exclusively limited to the above examples, but many variations are possible within the scope of the inventive idea defined by the claims.

The invention claimed is:

1. A method for separating and utilizing carbon dioxide, the method comprising: separating carbon dioxide from air being conducted to a building and/or from air being circulated in the building to reduce the level of carbon dioxide in indoor air of the building, wherein water is removed from the air being conducted to the building and/or from the air being circulated in the building; recovering the carbon dioxide; and conducting the carbon dioxide to a carbon dioxide treatment stage, where the carbon dioxide is treated by means of hydrogen in order to form a chemical compound.

2. The method according to claim 1, wherein hydrocarbon is formed in the carbon dioxide treatment stage.

3. The method according to claim 1, wherein methane ($CH_4$) is formed in the carbon dioxide treatment stage.

4. The method according to claim 1, wherein heat generated in the carbon dioxide treatment stage is conducted to the separating of carbon dioxide.

5. The method according to claim 1, wherein hydrogen is formed by electrolysis from the water.

6. The method according to claim 5, the hydrogen is conducted to the carbon dioxide treatment stage.

7. The method according to claim 5, wherein the hydrogen formed is conducted to a manufacture of an ammonia based compound.

8. The method according to claim 5, wherein the water removed in connection with the separation of carbon dioxide is conducted to the electrolysis.

9. The method according to claim 5, wherein the water produced in the carbon dioxide treatment stage is conducted to the electrolysis.

10. The method according to claim 5, wherein heat generated in the hydrogen formation is conducted to the separation of carbon dioxide.

11. The method according to claim 5, wherein oxygen produced in the hydrogen formation is conducted to the air being conducted to the building, to the air being circulated in the building and/or to the indoor air.

12. The method according to claim 1, further comprising treating the indoor air, in a manufacture of hydrocarbons, in a manufacture of hydrogen, and in combinations thereof.

13. An apparatus for separating and utilizing carbon dioxide, wherein the apparatus comprises: at least one separating device for separating carbon dioxide from air being conducted to a building and/or from air being circulated in the building to reduce the level of carbon dioxide in indoor air of the building; at least one set of means for arranging the treated air as the indoor air of the building; at least one carbon dioxide treatment stage, which comprises at least one treatment device and where the carbon dioxide is treated by means of hydrogen in order to form a chemical compound; at least one set of means for recovering the carbon dioxide from the separating device and for conducting it to the treatment stage; and at least one set of means for removing water from the air being conducted to the building and/or from the air being circulated in the building in connection with the carbon dioxide separating device.

14. The apparatus according to claim 13, wherein the apparatus comprises an electrolysis device for forming hydrogen from the water.

15. The apparatus according to claim 14, wherein the apparatus comprises means for conducting hydrogen from the electrolysis device to the carbon dioxide treatment stage.

* * * * *